United States Patent
Gandhi et al.

(10) Patent No.: US 9,974,770 B2
(45) Date of Patent: *May 22, 2018

(54) FORMULATIONS COMPRISING TRIPTAN COMPOUNDS

(71) Applicant: DR. REDDY'S LABORATORIES LIMITED, Hyderabad (IN)

(72) Inventors: Rajesh Gandhi, Sagar (IN); Sreekanth Manikonda, Visakhapatnam (IN); Arun Jana, Panna (IN); Sameer Shrinivas Kunte, Mumbai (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/434,814

(22) Filed: Feb. 16, 2017

(65) Prior Publication Data

US 2017/0157091 A1 Jun. 8, 2017

Related U.S. Application Data

(60) Division of application No. 14/925,564, filed on Oct. 28, 2015, now Pat. No. 9,610,280, which is a division of application No. 12/817,740, filed on Jun. 17, 2010, now Pat. No. 9,211,282, which is a continuation-in-part of application No. 12/816,904, filed on Jun. 16, 2010, now abandoned, and a continuation of application No. PCT/US2010/038838, filed on Jun. 16, 2010.

(60) Provisional application No. 61/292,206, filed on Jan. 5, 2010, provisional application No. 61/292,213, filed on Jan. 5, 2010.

(30) Foreign Application Priority Data

Sep. 25, 2009 (IN) .......................... 2337/CHE/2009
Oct. 27, 2009 (IN) .......................... 2607/CHE/2009

(51) Int. Cl.
*A61K 31/4045* (2006.01)
*A61K 9/00* (2006.01)
*A61K 47/26* (2006.01)

(52) U.S. Cl.
CPC ........ *A61K 31/4045* (2013.01); *A61K 9/0043* (2013.01); *A61K 47/26* (2013.01)

(58) Field of Classification Search
CPC ... A61K 31/4045; A61K 47/26; A61K 9/0043
See application file for complete search history.

(56) References Cited

U.S. PATENT DOCUMENTS

| | | | |
|---|---|---|---|
| 4,816,470 A | 3/1989 | Dowle et al. | |
| 4,994,483 A | 2/1991 | Oxford et al. | |
| 5,037,845 A | 8/1991 | Oxford | |
| 5,270,333 A | 12/1993 | Bays et al. | |
| 5,288,498 A | 2/1994 | Stanley et al. | |
| 5,307,953 A | 5/1994 | Regan | |
| 5,393,773 A | 2/1995 | Craig et al. | |
| 5,447,729 A | 9/1995 | Belenduik et al. | |
| 5,554,639 A | 9/1996 | Craig et al. | |
| 5,705,520 A | 1/1998 | Craig et al. | |
| 5,863,559 A | 1/1999 | Phillips et al. | |
| 6,020,001 A | 2/2000 | Phillips et al. | |
| 6,255,502 B1 | 7/2001 | Penkler et al. | |
| 6,294,192 B1 | 9/2001 | Patel et al. | |
| 6,368,627 B1 | 4/2002 | Phillips et al. | |
| 7,459,146 B2 | 12/2008 | Baran, Jr. et al. | |
| 7,497,214 B2 | 3/2009 | Hodson | |
| 7,524,510 B2 | 4/2009 | Arnold et al. | |
| 7,718,162 B2 | 5/2010 | Stefely et al. | |
| 8,268,791 B2 | 9/2012 | Maggio | |
| 8,715,715 B2 | 5/2014 | Ryoo et al. | |
| 8,883,728 B2 | 11/2014 | Maggio | |
| 2003/0013753 A1 | 1/2003 | Aung-Din | |

(Continued)

FOREIGN PATENT DOCUMENTS

| | | | |
|---|---|---|---|
| DE | 4314976 C1 | 10/1994 | |
| GB | 2162552 A | 2/1986 | |
| WO | WO 2010075465 A1 * | 7/2010 | ........... A61K 9/0043 |

OTHER PUBLICATIONS

International Search Report dated Apr. 6, 2011, for corresponding International Patent Application No. PCT/IB2010/001708.
Written Opinion dated Apr. 6, 2011, for corresponding International Patent Application No. PCT/IB2010/001708.
International Preliminary Report on Patentability for corresponding International Patent Application No. PCT/IB2010/001708, dated Dec. 22, 2011.
Decision of Rejection mailed by the Patent Office of Japan dated May 12, 2015, for corresponding Japanese patent application No. JP 2012-530344. (With English Translation).
Notice of Reasons for Rejection mailed by the Japanese Patent Office dated Jul. 1, 2014, for corresponding Japanese Patent Application No. JP 2012-530344. (With English Translation).
Office Action issued by the Canadian Patent Office dated Dec. 1, 2015, for corresponding Patent Application No. 2,775,404.

(Continued)

*Primary Examiner* — Sarah Pihonak
(74) *Attorney, Agent, or Firm* — Stites & Harbison, PLLC

(57) ABSTRACT

The invention provides a pharmaceutical composition for intranasal administration comprising a salt of sumatriptan or a physiologically acceptable solvate thereof, an alkyl glycoside or saccharide alkyl ester and optionally at least one pharmaceutically acceptable excipient, wherein the said composition provides $T_{max}$ value of less than 30 minutes upon said administration. Other aspects and embodiments are contemplated and described. The invention also provides a pharmaceutical composition for intranasal administration comprising a triptan, a pharmaceutically acceptable vehicle and a mucosal permeation enhancer, wherein upon said administration said composition provides a $T_{max}$ substantially equivalent to subcutaneous administration of said triptan. Other aspects and embodiments are contemplated and described.

20 Claims, 4 Drawing Sheets

(56) References Cited

U.S. PATENT DOCUMENTS

| | | |
|---|---|---|
| 2003/0185761 A1 | 10/2003 | Dugger, III |
| 2003/0190286 A1 | 10/2003 | Dugger, III |
| 2004/0248846 A1 | 12/2004 | Quay et al. |
| 2005/0084530 A1 | 4/2005 | Rao et al. |
| 2006/0002989 A1 | 1/2006 | Ahmed et al. |
| 2006/0045868 A1 | 3/2006 | Meezan et al. |
| 2006/0045869 A1 | 3/2006 | Meezan et al. |
| 2006/0046969 A1 | 3/2006 | Maggio |
| 2007/0298010 A1 | 12/2007 | Maggio |
| 2008/0200418 A1 | 8/2008 | Maggio |
| 2009/0047347 A1 | 2/2009 | Maggio |
| 2009/0163447 A1* | 6/2009 | Maggio ............... A61K 9/0043 514/103 |
| 2010/0160378 A1 | 6/2010 | Maggio |

OTHER PUBLICATIONS

GlaxoSmithKline K.K. IMIGRAN Nasal Spray 20, package insert 2007.

Office Action dated Oct. 18, 2016, mailed by the Russian Patent Office, for corresponding Patent Application No. 2012116452. (With English Translation).

Moore et al., "Safety, tolerability, and pharmacokinetics of sumatriptan in healthy subjects following ascending single intranasal doses and multiple intranasal doses", Cephalalgia, 1997, pp. 541 to 550, vol. 17.

Fuseau et al., "Clinical Pharmacokinetics of Intranasal Sumatriptan", Clin Pharmacokinet, 2002, pp. 801 to 811, vol. 41—issue No. 11, Adis International Limited.

Further Examination Report dated Jun. 11, 2014, for corresponding New Zealand Patent Application No. 599344.

Non-Final Office Action mailed by the USPTO dated Oct. 3, 2012, for corresponding U.S. Appl. No. 12/817,740.

Final Office Action mailed by the USPTO dated Jun. 28, 2013, for corresponding U.S. Appl. No. 12/817,740.

Non-Final Office Action mailed by the USPTO dated Dec. 8, 2014, for corresponding U.S. Appl. No. 12/817,740.

Final Office Action mailed by the USPTO dated Jun. 4, 2015, for corresponding U.S. Appl. No. 12/817,740.

Non-Final Office Action mailed by the USPTO dated Jan. 5, 2016, for corresponding U.S. Appl. No. 14/925,564.

Final Office Action mailed by the USPTO dated Jul. 6, 2016, for corresponding U.S. Appl. No. 14/925,564.

http://medical-dictionary.thefreedictionary.com/lyophilization.

* cited by examiner

FORMULATIONS COMPRISING TRIPTAN COMPOUNDS

INTRODUCTION

This application is a Divisional of U.S. patent application Ser. No. 14/925,564, filed Oct. 28, 2015, which is a Divisional of U.S. application Ser. No. 12/817,740 filed Jun. 17, 2010, now issued as U.S. Patent No. 9,211,282 on Dec. 15, 2015, which is a continuation-in-part of U.S. application Ser. No. 12/816,904, filed Jun. 16, 2010, and a continuation of International Application No. PCT/US10/38838, filed Jun. 16, 2010; which claims the benefit of U.S. Provisional Application Ser. No. 61/292,206, filed Jan. 5, 2010; U.S. Provisional Application Ser. No. 61/292,213, filed Jan. 5, 2010, Indian Provisional Application No. 2337/CHE/2009, filed Sep. 25, 2009 and Indian Provisional Application No. 2607/CHE/2009, filed Oct. 27, 2009.

The current therapies to treat migraine headaches include the administration of serotonin $5H_{1B/1D}$ receptor agonists collectively called as triptans, which chemically are tryptamine-based drugs. Sumatriptan was the first of these compounds to be developed, which offered improved efficacy and tolerability over ergot-derived compounds. The development of sumatriptan was quickly followed by a number of second generation triptans including zolmitriptan, naratriptan, and rizatriptan. Recent polls of migraineurs (people who suffer from migraines more than twice a month) suggest that more lipophilic formulations of other triptans, given orally, are still preferred over the sumatriptan nasal spray (IMITREX®). While these alternative triptans have slightly different binding affinities for the various $5HT_{1B/1D}$ receptors, the single guiding factor in success with these formulations seems to be the speed of action.

Sumatriptan is a selective 5-hydroxytryptamine ID ($5\text{-}HT_{1D}$) receptor agonist useful for treatment of migraine. Sumatriptan has a chemical name 1-[3-(2-dimethylaminoethyl)-1H-indole-5-yl]-N-methyl-methane sulphonamide, which has the following structure (I). Broadly, all the triptans are selective 5HT receptor agonists useful for treatment of migraine.

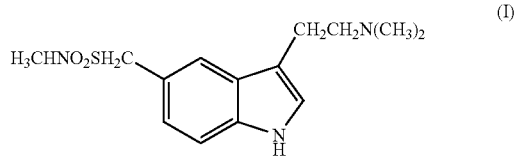

(I)

U.S. Pat. No. 5,705,520 describes 3-[2-(dimethylamino) ethyl]-N-methyl-1H-methanesulphonamide sulphate salt (2:1) and pharmaceutically acceptable solvates thereof, and pharmaceutical compositions containing the compound. The compound is useful in the treatment of conditions associated with cephalic pain, in particular migraine. The pharmaceutical compositions are particularly useful as intranasal formulations.

U.S. Pat. No. 5,554,639 discloses 3-[2-(dimethylamino) ethyl]-N-methyl-1H-indole-5-methanesulphonamide sulphate salt (2:1) and pharmaceutically acceptable solvates thereof. The compound is of use in the preparation of pharmaceutical compositions for use in the treatment of conditions associated with cephalic pain, in particular migraine, wherein an aqueous solution has a pH range of 5 to 7.

U.S. Patent Application Publication No. 2007/0298010 discloses alkylglycoside-containing compositions and methods for increasing the stability, reducing the aggregation and immunogenicity, increasing the biological activity, and reducing or preventing fibrillar formation of a peptide, polypeptide, or variant thereof, for example insulin, Peptide T, or analogs thereof.

International Application No. WO 2006/025882 discloses a composition including a surfactant, at least one alkyl glycoside and/or saccharide alkyl ester, and a drug. The surfactant compositions when admixed with a drug are non-toxic and non-irritating, while stabilizing and increasing the bioavailability of the drug. The invention also provides compositions that enhance absorption of drugs via oral, ocular, nasal, nasolacrimal, inhalation, pulmonary, oral cavity (sublingual or buccal) or CSF delivery route of a patient. The drugs include glucagon and exendin-4.

Pharmaceutical preparations containing sumatriptan or salts of sumatriptan are described in U.S. Pat. Nos. 4,816,470, 4,994,483, 5,037,845, 5,270,333, 5,288,498, 5,307,953, 5,393,773, 5,447,729, 5,554,639, 5,705,520, 5,863,559, 6,020,001, 6,255,502, 6,294,192, and 6,368,627, U.S. Patent Application Publication Nos. 2003/0013753, 2003/0185761, and 2003/0190286, International Application Publication Nos. WO 98/02186 and WO 01/39836, and German Patent No. 4314976.

Great Britain Patent Specification No. 2162522 describes physiologically acceptable salts of 3-[2-(dimethylamino) ethyl]-N-methyl-1H-indole-5-methane sulphonamide (sumatriptan), which are the succinate, hemisuccinate, fumarate, benzoate, methanesulphonate, and hydrochloride salts.

U.S. Patent Application Publication No. 2006/002989 discloses pharmaceutical compositions comprising sumatriptan succinate and sodium caprate for increased absorption of sumatriptan succinate across biological membranes. The invention is also directed to methods of making the pharmaceutical compositions and uses thereof.

Commercially, sumatriptan nasal products sold under the trade name IMITREX®, supplied as a nasal spray containing 5, 10 or 20 mg of sumatriptan in a 100 μL unit dose aqueous buffered solution containing monobasic potassium phosphate NF, anhydrous dibasic sodium phosphate USP, sulfuric acid NF, sodium hydroxide NF, and purified water USP. The pH of the solution is approximately 5.5. The osmolality of the solution is 372 or 742 m-Osmol for the 5 and 20 mg nasal sprays.

The existing marketed formulations of triptans have onset of action about 30 minutes or less. Thereby It is highly desirable to develop a formulation where there would be a onset of action quicker than existing formulation, after dosing, so that there will be faster relief of pain in migraine.

There is a long felt need to develop alternate triptan formulations that have an increased speed or onset of action as well as an improved permeability over the earlier triptan formulations and meeting the unmet requirements in the treatment of migraine attacks.

SUMMARY

The present invention provides a pharmaceutical composition comprising a salt of sumatriptan or a physiologically acceptable solvate thereof, a mucosal permeation enhancer and optionally at least one pharmaceutically acceptable excipient, wherein the said composition provides $T_{max}$ value of less than 30 minutes upon said administration.

The present invention provides a pharmaceutical composition comprising a salt of sumatriptan or a physiologically acceptable solvate thereof, an alkylglycoside or saccharide alkyl ester and optionally at least one pharmaceutically acceptable excipient, wherein the said composition provides $T_{max}$ value of less than 30 minutes upon said administration.

Preferably, an aspect of the present invention specifically provides a pharmaceutical composition comprising a citrate salt of sumatriptan or a physiologically acceptable solvate thereof, an alkylglycoside or saccharide alkyl ester, and optionally at least one pharmaceutically acceptable excipient.

In another aspect the present invention provides a method of treating a human suffering from or susceptible to cephalic pain which comprises administration of a composition comprising a salt of sumatriptan or a physiologically acceptable solvate thereof, an alkyl glycoside or saccharide alkyl ester and optionally at least one pharmaceutically acceptable excipient, wherein the said composition provides $T_{max}$ value of less than 30 minutes upon said administration.

Another aspect of the invention provides a pharmaceutical composition for intranasal administration comprising a triptan, a pharmaceutically acceptable vehicle and a mucosal permeation enhancer, wherein upon said administration said composition provides a $T_{max}$ substantially equivalent to subcutaneous administration of said triptan.

Another aspect of the invention provides a method of treating or mitigating deseases or conditions suitable for treatment with triptan compounds in a subject in need thereof, said method comprising intranasally administering to said subject a pharmaceutical composition comprising a triptan, a pharmaceutically acceptable vehicle and a mucosal permeation enhancer, wherein upon said administration, said composition provides a $T_{max}$ substantially equivalent to subcutaneous administration of said triptan.

Another aspect of the invention provides a method of treating or mitigating deseases or conditions suitable for treatment with triptan compounds in a subject in need thereof, said method comprising intranasally administering to said subject a pharmaceutical composition comprising a triptan, a pharmaceutically acceptable vehicle and a mucosal permeation enhancer, wherein upon said administration, said composition provides i) a $C_{max}$ at a time $T_{max}$, ii) $C_{max2}$ at a time $T_{max2}$, iii) a $C_{min}$ at a time of $T_{min}$, and iv) a ratio of $C_{max2}$ to $AUC_{Tmin-inf}$, said $T_{min}$ being later than said $T_{max}$ and earlier than said $T_{max2}$, said $C_{max}$ and said $T_{max}$ being characteristic of subcutaneous administration and said $AUC_{Tmin-inf}$ being characteristic of intranasal administration without said mucosal permeation enhancer.

DETAILED DESCRIPTION

Figure 1:
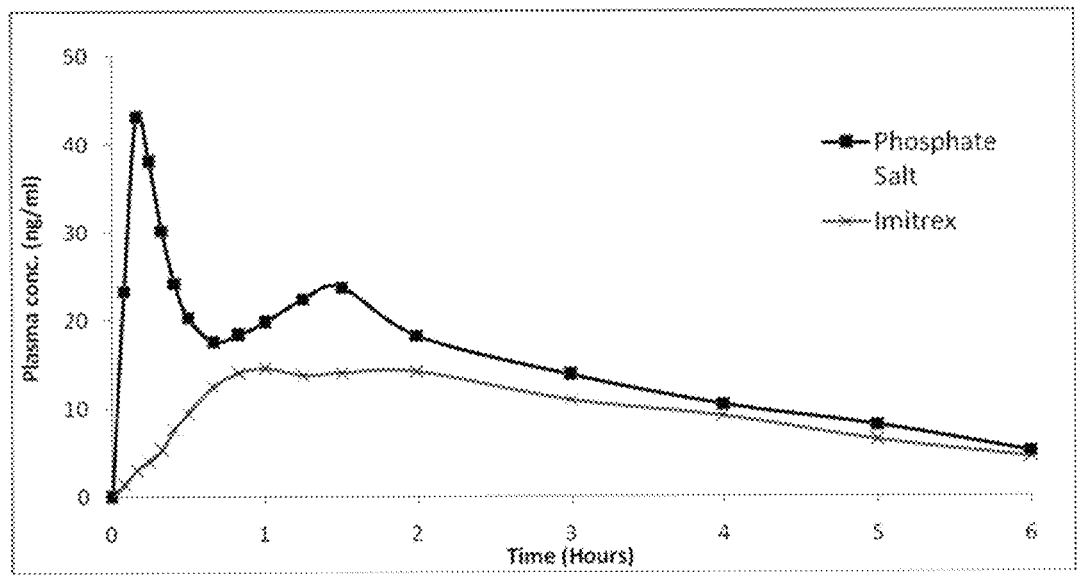
FIG.-1 shows a comparison of the average plasma levels of all patients at the various time points as indicated for the Imitrex® nasal spray reference and Phosphate salt of Sumatriptan pharmaceutical composition described herein.

Definitions:
'Salt of sumatriptan' is intended to include, but not limited to, any of the following salts of sumatriptan: sulphate salt, citrate salt, phosphate salt, maleate salt, formate salt and acetate salt.

Other examples of salts of sumatriptan are, but not limited to, hydrochloride, hydrobromide, nitrate, mesylate, benzoate and succinate.

'Salt of sumatriptan' is also intended to include above defined salt of Sumatriptan formed either externally or in situ during the preparation of the composition, by addition of the corresponding acid.

'Salts or a derivative of citric acid' indicates a source of citric acid that can be selected from the group containing citric acid anhydrous, citric acid monohydrate, trisodium citrate dihydrate, monosodium citrate and citric acid solutions.

'Commerical formulation' means 'Imitrex® (Sumatriptan) nasal spray, 20 mg per 100 microliters), manufactured by GlaxoSmithKline', 'Physiologically acceptable solvates' includes 'their hydrates thereof' as well.

'Quantity sufficient' can be defined as the minimum amount of the solvent required for dissolving the active ingredient.

'Triptan' includes sumatriptan, rizatriptan, naratriptan, zolmitriptan, eletriptan, almotriptan, frovatriptan and/or a pharmaceutically acceptable salt, solvate, hydrate, polymorph, prodrug or mixtures thereof.

'Area under the curve' or "AUC" is the area as measured under a plasma drug concentration curve. Often, the AUC is specified in terms of the time interval across which the plasma drug concentration curve is being integrated, for instance $AUC_{start-finish}$. Thus, $AUC_{0-24}$ refers to the AUC obtained from integrating the plasma concentration curve over a period of zero to 24 hours, where zero conventionally represents the time of administration of the drug or dosage form thereof to a patient.

$AUC_{0-2}$ refers to the AUC obtained from integrating the plasma concentration curve over a period of zero to 2 hours, where zero conventionally represents the time of administration of the drug or dosage form thereof to a patient. $AUC_{0-6}$ refers to the AUC obtained from integrating the plasma concentration curve over a period of zero to 6 hours, where zero conventionally represents the time of administration of the drug or dosage form thereof to a patient. $AUC_t$ refers to area under the plasma concentration curve from hour "0" to the last detectable concentration at time "t", calculated by the trapezoidal rule. $AUC_{inf}$ refers to the AUC value extrapolated to infinity, calculated as the sum of $AUC_t$ and the area extrapolated to infinity, calculated by the concentration at time t (Ct) divided by $K_{ef}$. (If the $t_{1/2}$ value was not estimable for a subject, the mean $t_{1/2}$ value of that treatment was used to calculate $AUC_{inf}$). "Mean, single dose, area under a plasma concentration-time curve $AUC_{inf}$" means the mean $AUC_{inf}$ obtained over several patients or by multiple administrations to the same patient on different occasions with sufficient washout in between dosings to allow drug levels to subside to pre-dose levels, following a single administration of a dosage form to each patient. "Partial AUC" means area under the curve specified in terms of the time interval across which the plasma drug concentration curve is being integrated, for instance $AUC_{0-Tmax}$.

'C' means the concentration of drug in blood plasma, or serum, of a subject, generally expressed as mass per unit volume, typically nanograms (ng) per milliliter. For convenience, this concentration may be referred to herein as "drug plasma concentration", "plasma drug concentration" or "plasma concentration". The plasma drug concentration at any time following drug administration is referenced as $C_{time}$, as in $C_{9h}$ or $C_{24h}$, etc. A maximum plasma concentration obtained following administration of a dosage form obtained directly from the experimental data without interpolation is referred to as $C_{max}$. The average or mean plasma concentration obtained during a period of interest is referred to as $C_{avg}$ or $C_{mean}$. "Mean, single dose, maximum plasma concentration $C_{max}$" means the mean $C_{max}$ obtained over several patients or multiple administrations to the same patient with sufficient washout in between dosings to allow drug levels to subside to pre-dose levels etc., following a single administration of a dosage form to each patient.

$C_{max2}$ denotes a second maximum of concentration of drug in blood plasma, or serum, of a subject, generally expressed as mass per unit volume, typically nanograms (ng) per milliliter that occurs at time after administration later than $C_{max}$.

'$C_{min}$' means the minimum concentration of drug in blood plasma, or serum, of a subject, generally expressed as mass per unit volume, typically nanograms (ng) per milliliter that occurs between $C_{max}$ and $C_{max2}$.

'$T_{min}$' is the time after administration of the drug when the drug concentration has value of $C_{min}$.

$AUC_{Tmin-inf}$ refers to area under the plasma concentration curve from '$T_{min}$' to infinity. Here $AUC_{inf}$ refers to the AUC value extrapolated to infinity, calculated as the sum of $AUC_{Tmin-t}$ and the area extrapolated to infinity, calculated by the concentration at time t (Ct) divided by $K_{el}$.

'Mean, single dose, time to maximum plasma concentration $T_{max}$' is the mean time elapsed from administration to a patient of a dosage form comprising a drug to the time at which the $C_{max}$ for that drug is obtained over several patients or multiple administrations to the same patient to the same patient with sufficient washout in between dosings to allow drug levels to subside to pre-dose levels, etc., following a single administration of the dosage form to each patient, and obtained directly from the experimental data without interpolation.

'Plasma drug concentration curve' or 'drug plasma concentration curve', or "plasma concentration curve" or "plasma profile" or "plasma concentration profile" refer to the curve obtained by plotting plasma drug concentration or drug plasma concentration, or plasma concentration versus time. Usually, the convention is that the zero point on the time scale (conventionally on the X-axis) is the time of administration of the drug or dosage form comprising the drug to a patient.

The term 'pharmaceutically acceptable excipient' is used to describe a substance which does not have inherent pharmacological activity and is used as an inactive ingredient.

'Mucosal permeation enhancer' denotes any penetration enhancer that assists in penetration of the drug via mucosal membrane. It includes, but not limited to, alkylglycoside or saccharide alkyl ester.

The term 'substantially equivalent to subcutaneous administration' means that one skilled in the art of pharmacology and/or pharmacokinetics would recognize the shape and time profile of the blood/concentration curve as having characteristics of subcutaneous administration of the drug.

The term 'about' denotes a range of value ranging from −10% of the value it modifies to +10% of the value it modifies, with the proviso that such claim construction does not preclude application of broader equivalent values.

The term 'alkylglycoside or saccharide alkyl ester' includes, but is not limited to, dodecyl maltoside (1-O-n-Dodecyl-β-D-Maltopyranoside), tridecyl maltoside, sucrose monododecanoate, sucrose monotridecanoate, and sucrose monotetradecanoate.

In general, alkylglycosides or saccharide alkyl esters useful in the present invention include, but are not limited to: alkyl glycosides, such as octyl-, nonyl-, decyl-, undecyl-, dodecyl-, tridecyl-, tetradecyl-, pentadecyl-,hexadecyl-, heptadecyl-, and octadecyl-[alpha]- or [beta]-D-maltoside, -glucoside or -sucroside (synthesized according to Koeltzow and Urfer; Anatrace Inc., Maumee, Ohio; Calbiochem, San Diego, Calif.; Fluka Chemie, Switzerland); alkyl thiomaltosides, such as heptyl, octyl, dodecyl-, tridecyl-, and tetradecyl-[beta]-D-thiomaltoside (synthesized according to Defaye, J. and Pederson, C, "Hydrogen Fluoride, Solvent and Reagent for Carbohydrate Conversion Technology" in *Carbohydrates as Organic Raw Materials*, 247-265 (F. W. Lichtenthaler, ed.) VCH Publishers, New York (1991); Ferenci, T., J. Bacteriol, 144:7-11 (1980)); alkyl thioglucosides, such as heptyl- or octyl 1-thio[alpha]- or [beta]-D-glucopyranoside (Anatrace, Inc., Maumee, Ohio; see Saito, S. and Tsuchiya, T. Chem. Pharm. Bull. 33:503-508 (1985)); alkyl thiosucroses (synthesized according to, for example, Binder, T. P. and Robyt, J. F., Carbohydr. Res. 140:9-20 (1985)); alkyl maltotriosides (synthesized according to Koeltzow and Urfer); long chain aliphatic carbonic acid amides of sucrose [beta]-amino-alkyl ethers; (synthesized according to Austrian Patent 382,381 (1987); derivatives of palatinose and isomaltamine linked by amide linkage to an alkyl chain (synthesized according to Kunz, M., "Sucrose-based Hydrophilic Building Blocks as Intermediates for the Synthesis of Surfactants and Polymers" in Carbohydrates as Organic Raw Materials, 127-153); derivatives of isomaltamine linked by urea to an alkyl chain (synthesized according to Kunz); long chain aliphatic carbonic acid ureides of sucrose [beta]-amino-alkyl ethers (synthesized according to Gruber and Greber, pp. 95-116); and long chain aliphatic carbonic acid amides of sucrose [beta]-amino-alkyl ethers (synthesized according to Austrian Patent No. 382,381 (1987), *Chemical Abstracts*, 108: 1 14719 (1988) and Gruber and Greber, pp. 95-116). Surfactants of the alkylglycoside and/or sucrose ester types have characteristic hydrophilic-lipophilic balance (HLB) numbers, which can be calculated or determined empirically (M. J. Schick, *Nonionic Surfactants*, Marcel Dekker, Inc., New York, p. 607, 1967). Examples of suitable penetration enhancers are also disclosed in US20060046962, US20060045869, US20060045868, US20090163447, US20090047347, US20080299079, US20080200418, US20060046969, which are incorporated herein by reference in their entirety and for the purpose stated.

Absorption and permeation of a drug involves passage of the drug across biological membranes whereby a cell, tissue or organ takes up the drug. Absorption/permeation is also referred to as the rate and extent to which a drug leaves its site of administration. The physicochemical properties of the molecules in the pharmaceutical composition as well as that of the membranes affect the absorption of drugs across membranes.

Biological membranes are sheets of tissue that include but are not limited to membranes that provide a pliable surface lining for protecting or partitioning organs and structures in the body. As used herein, a biological membrane is an epithelial membrane. Epithelial membranes include but are not limited to coverings or linings of the outer layer of skin and some internal organs, e.g., digestive, respiratory, reproductive and urinary systems. Epithelial membranes include the lining of body cavities.

Epithelial membranes include but are not limited to oral, buccal, sublingual, gingival, palatal, nasal, nasopharynxal, oropharynxal, conjunctival, transdermal, vaginal, and gastrointestinal membranes. In one embodiment of the invention, the epithelial membrane is the nasal membrane.

Absorption/permeation enhancers are agents that increase drug absorption and permeation across biological membranes. Absorption/permeation enhancers for use in pharmaceutical composition of the present invention include alkylglycosides but are not limited to alkylglycosides only; enhancers also may be materials such as sodium caprate, sodium caprylate, sodium laurate, sodium lauryl sulphate, and combinations thereof.

The term 'transmucosal' relates to a delivery system through mucosa, the mucosa may be of oral, buccal, sublingual, gingival, palatal, nasal, nasopharynxal, oropharynxal, conjunctival, vaginal, and gastrointestinal membranes.

Therapeutically effective amounts of active ingredient can be provided in the form of a pharmaceutical composition in the form of suspensions, emulsions, solutions, aerosols, powders, and the like. All such formulations are included herein without limitation.

The present invention provides a pharmaceutical composition comprising a salt of sumatriptan or a physiologically acceptable solvate thereof, a mucosal permeation enhancer and optionally at least one pharmaceutically acceptable excipient, wherein the said composition provides $T_{max}$ value of less than 30 minutes upon said administration.

The present invention provides a pharmaceutical composition comprising a salt of sumatriptan or a physiologically acceptable solvate thereof, an alkylglycoside or saccharide alkyl ester and optionally at least one pharmaceutically acceptable excipient, wherein the said composition provides $T_{max}$ value of less than 30 minutes upon said administration.

Preferably, according to the above aspect, the present invention provides a pharmaceutical composition comprising a sulphate salt of sumatriptan or a physiologically acceptable solvate thereof, an alkylglycoside or saccharide alkyl ester and optionally at least one pharmaceutically acceptable excipient.

Preferably, according to the above aspect, the present invention provides a pharmaceutical composition comprising a citrate salt of sumatriptan or a physiologically acceptable solvate thereof, an alkylglycoside or saccharide alkyl ester and optionally at least one pharmaceutically acceptable excipient.

Preferably, according to the above aspect, the present invention provides a pharmaceutical composition comprising a phosphate salt of sumatriptan or a physiologically acceptable solvate thereof, an alkylglycoside or saccharide alkyl ester and optionally at least one pharmaceutically acceptable excipient.

Preferably, according to the above aspect, the present invention provides a pharmaceutical composition comprising a maleate salt of sumatriptan or formate salt of sumatriptan or acetate salt of sumatriptan, or a physiologically acceptable solvate thereof, an alkylglycoside or saccharide alkyl ester, and optionally at least one pharmaceutically acceptable excipient.

According to the above aspect, the present invention provides a pharmaceutical composition comprising a salt of sumatriptan or a physiologically acceptable solvate thereof, an alkylglycoside or saccharide alkyl ester, and optionally at least one pharmaceutically acceptable excipient, the composition being adjusted to have a pH in the range of about 4 to about 8.

According to the above aspect, the present invention provides a pharmaceutical composition comprising a salt of sumatriptan or a physiologically acceptable solvate thereof, an alkylglycoside or saccharide alkyl ester, and optionally at least one pharmaceutically acceptable excipient, the composition being adjusted to have a pH in the range of about 4.5 to about 7.5.

According to the above aspect, the present invention provides a pharmaceutical composition comprising a salt of sumatriptan or a physiologically acceptable solvate thereof, an alkylglycoside or saccharide alkyl ester, and optionally at least one pharmaceutically acceptable excipient, the composition being adjusted to have a pH in the range of about 7.1 to about 9.

In the above aspect, $C_{max}$ values ranges from about 14 to about 214 ng/m L.

Preferably, according to the above aspect, the present invention specifically provides a pharmaceutical composition comprising a citrate salt of sumatriptan or a physiologically acceptable solvate thereof, an alkylglycoside or saccharide alkyl ester, and optionally at least one pharmaceutically acceptable excipient, the composition being adjusted to have a pH in the range of about 4 to about 8.

Preferably, according to the above aspect, the present invention provides a pharmaceutical composition comprising a citrate salt of sumatriptan or a physiologically acceptable solvate thereof, an alkylglycoside or saccharide alkyl ester, and optionally at least one pharmaceutically acceptable excipient, the composition being adjusted to have a pH in the range of about 4.5 to about 6.5.

Preferably, according to the above aspect, the present invention specifically provides a pharmaceutical composition comprising a phosphate salt of sumatriptan or a physiologically acceptable solvate thereof, an alkylglycoside or saccharide alkyl ester, and optionally at least one pharmaceutically acceptable excipient, the composition being adjusted to have a pH in the range of about 4.5 to about 8.

Preferably, according to the above aspect, the present invention specifically provides a pharmaceutical composition comprising a sulphate salt of sumatriptan or a physiologically acceptable solvate thereof, an alkylglycoside or saccharide alkyl ester, and optionally at least one pharmaceutically acceptable excipient, the composition being adjusted to have a pH in the range of about 4.5 to about 8.

Preferably, the above composition is adjusted to a pH in the range of about 5 to about 6.

In the above aspect, said mucosal permeation enhancer is present in a concentration of from about 0.02 to about 3.0%.

Preferably, in the above aspect, said mucosal permeation enhancer is present in a concentration of from about 0.05 to about 2.5%.

Preferably, in the above aspect, said mucosal permeation enhancer is present in a concentration of from about 0.1 to about 2.0%.

An aspect of the present invention provides a pharmaceutical composition comprising a salt of sumatriptan or a physiologically acceptable solvate thereof, dodecyl maltoside, and optionally at least one pharmaceutically acceptable excipient.

In the above aspect, the said composition provides $T_{max}$ value of less than 30 minutes upon said administration.

In the above aspect, the said composition provides $T_{max}$ value of less than or equal to 15 minutes upon said administration.

An aspect of the present invention provides transmucosal formulations comprising a salt of sumatriptan or a physiologically acceptable solvate thereof, an alkylglycoside or saccharide alkyl ester, and optionally at least one pharmaceutically acceptable excipient.

In the above aspect, the said composition provides $T_{max}$ value of less than 30 minutes upon said administration.

In the above aspect, the said composition provides $T_{max}$ value of less than or equal to 15 minutes upon said administration.

An aspect of the invention provides a pharmaceutical composition comprising a salt of sumatriptan or a physiologically acceptable solvate thereof, an alkylglycoside or saccharide alkyl ester, and optionally at least one pharmaceutically acceptable excipient, for delivery by the nasal route.

In the above aspect, the said composition provides $T_{max}$ value of less than 30 minutes upon said administration.

In the above aspect, the said composition provides $T_{max}$ value of less than or equal to 15 minutes upon said administration.

An aspect of the present invention provides a pharmaceutical composition comprising a salt of sumatriptan or a physiologically acceptable solvate thereof, an alkylglycoside or saccharide alkyl ester, and optionally at least one pharmaceutically acceptable excipient, for delivery by the subcutaneous route.

In the above aspect, the said composition provides $T_{max}$ value of less than 30 minutes upon said administration.

In the above aspect, the said composition provides $T_{max}$ value of less than or equal to 15 minutes upon said administration.

In the above aspect the salt of sumatriptan or a physiologically acceptable solvate thereof, is preferably sulphate salt, citrate salt or phosphate salt of sumatriptan or a physiologically acceptable solvate thereof, an alkylglycoside or saccharide alkyl ester, and optionally at least one pharmaceutically acceptable excipient, wherein the composition upon nasal administration shows the following one or more pharmacokinetic parameters:

$T_{max}$ value of less than or equal to about 15 minutes, and/or at least three fold reduction in $T_{max}$ values when compared with that of commercial formulation, and/or at least three fold increase in $C_{max}$ value when compared with that of commercial formulation, and/or at least one fold reduction in $AUC_{0-Tmax}$ value when compared with that of commercial formulation, and/or at least one fold increase in $AUC_{0-Tmax}$ value when compared with that of similar composition comprising sulphate salt, and/or at least one fold increase in $AUC_{0-inf}$ value when compared with that of commercial formulation, and/or the ratio of $C_{max}$ to $AUC_{0-inf}$ is at least about 0.3.

In one aspect the composition comprising citrate salt of sumatriptan or a physiologically acceptable solvate thereof, an alkylglycoside or saccharide alkyl ester, and optionally at least one pharmaceutically acceptable excipient wherein the composition upon nasal administration shows the $T_{max}$ value of less than or equal to about 15 minutes.

Another aspect of the present invention provides a method of treating migraine attacks by nasal administration of the formulation comprising a sumatriptan salt or its physiologically acceptable solvate thereof and at least about 0.1% of alkyl glycoside.

In the above aspect, the alkyl glycoside is selected from dodecyl maltoside, tridecyl maltoside, tetradecyl maltoside, octyl decyl alpha or beta maltoside.

Preferably, the salt of sumatriptan is citrate salt.
Preferably, the salt of sumatriptan is phosphate salt.
Preferably, the salt of sumatriptan is sulphate salt.

In another aspect the present invention provides a method of treating a human suffering from or susceptible to cephalic pain which comprises administration of a composition comprising a salt of sumatriptan or a physiologically acceptable solvate thereof, an alkyl glycoside or saccharide alkyl ester and optionally at least one pharmaceutically acceptable excipient.

In the above aspect, the said composition provides $T_{max}$ value of less than 30 minutes upon said administration.

In the above aspect, the said composition provides $T_{max}$ value of less than or equal to 15 minutes upon said administration.

In the above method, the composition was adjusted to a pH in the range of about 4 to about 8, preferably about 4.5 to about 7.5.

Yet another aspect of the present invention provides a method of treating a human suffering from or susceptible to cephalic pain which comprises administration of a composition comprising citrate salt of sumatriptan or a physiologically acceptable solvate thereof, an alkyl glycoside or saccharide alkyl ester and optionally at least one pharmaceutically acceptable excipient.

In the above aspect, the said composition provides $T_{max}$ value of less than 30 minutes upon said administration.

In the above aspect, the said composition provides $T_{max}$ value of less than or equal to 15 minutes upon said administration.

In the above method, the composition is adjusted to a pH in the range of about 4 to about 8, preferably about 4.5 to about 6.5, still further preferably about 5 to about 6.

In an aspect, the present invention provides transmucosal formulations comprising a salt of sumatriptan or a pharmaceutically acceptable solvates thereof. In an embodiment, the invention provides sumatriptan pharmaceutical composition comprising sumatriptan or a pharmaceutically acceptable salt, solvate, hydrate, polymorph, prodrug or mixtures thereof, and an alkylglycoside. One embodiment also includes processes for preparing such formulations and method of using such formulations for treating conditions associated with cephalic pain in mammals, specifically migraine.

An aspect of the present invention provides a transmucosal delivery system comprising a salt of sumatriptan or a physiologically acceptable solvate thereof, and a mucosal permeation enhancer.

An aspect of the present invention provides intranasal delivery systems comprising a salt of sumatriptan or a physiologically acceptable solvate thereof, and a mucosal permeation enhancer. The intranasal composition may be provided in a liquid form or in the form of dry powder. The liquid form can be solutions applied directly to the nasal cavity by conventional means, for example with a dropper, pipette or a spray or as solutions using pressurized metered-dose inhalers (pMDI), or as dry powders using dry powder inhaler devices (DPIs). Alternatively the formulation may also be administered by breath actuated inhalers (BDIs). The dry powder form can be a spray dried composition or a freeze dried composition having the drug in a micronized form and alternatively the drug can be in a microparticulate or a nanoparticulate form.

Further aspect of the present invention provides intranasal delivery systems comprising a salt of sumatriptan or a physiologically acceptable solvate thereof, and a mucosal permeation enhancer.

Further aspect of the invention provides compositions comprising a salt of sumatriptan, wherein the composition is formulated for administration into the circulatory system of a subject via the oral, ocular, nasolacrimal, inhalation, pulmonary, sublingual, buccal or CSF delivery route.

An aspect of the present invention provides an aerosol formulation comprising a salt of sumatriptan or a physiologically acceptable solvate thereof, and a mucosal permeation enhancer as a solution in a propellant administered using pressurized metered-dose inhalers (pMDI) or by breath actuated inhalers (BDIs).

In the present invention, the inventors have surprisingly found that the use of a mucosal permeation enhancer in the pharmaceutical composition comprising a salt of sumatriptan or a physiologically acceptable solvate thereof, increases permeation through mucosa to enhance drug absorption, and provides an improved pharmacokinetic profile with simultaneous improvement in the onset of action and enhanced residence time which could facilitate more amounts of drug exposure to the absorption site, thus a possibility of enhanced absorption and improved bioavailability.

In a further aspect, the invention provides the use of a salt of sumatriptan or a physiologically acceptable solvate thereof, in the preparation of a medicament for use in the treatment of conditions associated with cephalic pain such as cluster headache, chronic paroxysmal hemi-crania, headache associated with vascular disorders, headache associated with substances or their withdrawal (for example drug withdrawal), tension headache, and in particular, migraine.

In another embodiment, a pharmaceutical composition comprising a salt of sumatriptan or a physiologically acceptable solvate thereof and an alkylglycoside or saccharide alkyl ester adapted for intranasal administration will be in the form of an aqueous solution.

In another embodiment a pharmaceutical composition comprising salt of sumatriptan or a physiologically acceptable solvate thereof and an alkylglycoside or saccharide alkyl ester adapted for intranasal administration will be in the powder form.

In the above embodiment, the salt is selected from sulphate, phosphate, citrate, maleate, formate, acetate or succinate.

In the above embodiment the salt is preferably citrate salt.

In the above embodiment the salt is preferably phosphate salt.

In the above embodiment the salt is preferably sulphate salt.

Another aspect of the invention provides a pharmaceutical composition for intranasal administration comprising a triptan, a pharmaceutically acceptable vehicle and a mucosal permeation enhancer, wherein upon said administration said composition provides a $T_{max}$ substantially equivalent to subcutaneous administration of said triptan.

In one embodiment of the above aspect of the invention, the mucosal permeation enhancer is not a cyclodextrin.

In the above aspect, said mucosal permeation enhancer is present in a concentration of from about 0.02 to about 3.0%.

Preferably, in the above aspect, said mucosal permeation enhancer is present in a concentration of from about 0.05 to about 2.5%.

Preferably, in the above aspect, said mucosal permeation enhancer is present in a concentration of from about 0.1 to about 2.0%.

In the above aspect, said $T_{max}$ ranges from about 4 to about 15 minutes.

Specifically contemplated is a formulation for intranasal administration and related method of administration which provides biphasic blood/concentration curve.

In accordance with the above aspect, said composition provides a $C_{max2}$ at a time of $T_{max2}$, said $T_{max2}$ being later than said $T_{max}$.

In the above aspect, said composition provides a $C_{min}$ at a time of $T_{min}$, said $T_{min}$ being later than said $T_{max}$ and earlier than said $T_{max2}$.

In the above aspect, said $T_{max}$ ranges from about 4 to about 15 minutes.

In accordance with the above aspect, said mucosal permeation enhancer is alkyl glycoside or saccharide alkyl ester.

In the above aspect, said alkyl glycoside or saccharide alkyl ester is selected from (1-O-n-Dodecyl-β-D-Maltopyranoside), tridecyl maltoside, sucrose monododecanoate, sucrose monotridecanoate and sucrose monotetradecanoate.

Examples of suitable penetration enhancers are disclosed in US20060046962, US20060045869, US20060045868, US20090163447, US20090047347, US20080299079, US20080200418, US20060046969, which are incorporated herein by reference for the purpose stated.

In the above aspect, said triptan compound is sumatriptan, a pharmaceutically acceptable salt thereof, or a pharmaceutically acceptable solvate thereof.

In the above aspect, said pharmaceutical composition provides i) a $C_{max}$ at a time $T_{max}$, ii) $C_{max2}$ at a time $T_{max2}$, iii) a $C_{min}$ at a time of $T_{min}$, and iv) a ratio of $C_{max2}$ to $AUC_{Tmin-inf}$, said $T_{min}$ being later than said $T_{max}$ and earlier than said $T_{max2}$, said $C_{max}$ and said $T_{max}$ being characteristic of subcutaneous administration and said $AUC_{Tmin-inf}$ being characteristic of intranasal administration without said mucosal permeation enhancer.

In the above aspect, $T_{max}$ ranges from about 4 to about 15 minutes.

In the above aspect, $T_{max2}$ ranges from about 30 to about 120 minutes.

In the above aspect, $C_{max}$ ranges from about 14 to about 214 ng/mL.

In the above aspect, $C_{max2}$ ranges from about 9 to about 80 ng/m L.

In the above aspect, said pharmaceutically acceptable vehicle is a liquid.

In the above aspect, said pharmaceutically acceptable vehicle is a dry powder, or a mixture of dry powder with a liquid. Examples of suitable propellants are described, for example, U.S. Pat. Nos. 7,718,162, and 7,459,146, which are incorporated herein by reference in their entirety and for the purpose stated. Any suitable device may be used for intranasal administration of the compositions described herein. Methods for selecting suitable delivery devices are described, for example, I U.S. Pat. No. 7,659,725, which is incorporated herein by reference in its entirety and for the purpose stated.

The pharmaceutically acceptable vehicle may also be a liquid or pressurized liquid. Any device known in the art for intranasal administration may be used to deliver the pharmaceutical composition of the present invention. An example of suitable device is described in U.S. Pat. No. 7,497,214, which is incorporated herein by reference for the purpose stated.

Yet another aspect of the invention provides a method of treating or mitigating deseases or conditions suitable for treatment with triptan compounds in a subject in need thereof, said method comprising intranasally administering to said subject a pharmaceutical composition comprising a triptan, a pharmaceutically acceptable vehicle and a mucosal permeation enhancer, wherein upon said administration, said composition provides a $T_{max}$ substantially equivalent to subcutaneous administration of said triptan.

In the above aspect said $T_{max}$ ranges from about 4 to about 15 minutes.

In the above aspect, said composition provides a $C_{max2}$ at a time of $T_{max2}$, said $T_{max2}$ being later than said $T_{max}$.

In the above aspect, said composition provides a $C_{min}$ at a time of $T_{min}$, said $T_{min}$ being later than said $T_{max}$ and earlier than said $T_{max2}$.

In the above aspect, said mucosal permeation enhancer is alkyl glycoside or saccharide alkyl ester.

In the above aspect, said alkyl glycoside or saccharide alkyl ester is selected from (1-O-n-Dodecyl-β-D-Maltopyranoside), tridecyl maltoside, sucrose monododecanoate, sucrose monotridecanoate and sucrose monotetradecanoate.

Another embodiment provides a method of treating or mitigating deseases or conditions suitable for treatment with triptan compounds in a subject in need thereof, said method comprising intranasally administering to said subject a pharmaceutical composition comprising a triptan, a pharmaceutically acceptable vehicle and a mucosal permeation enhancer, wherein upon said administration, said composition provides a $C_{max}$ at a time $T_{max}$, ii) $C_{max2}$ at a time $T_{max2}$, iii) a $C_{min}$ at a time of $T_{min}$, and iv) a ratio of $C_{max2}$ to $AUC_{Tmin-inf}$, said $T_{min}$ being later than said $T_{max}$ and earlier than said $T_{max2}$, said $C_{max}$ and said $T_{max}$ being characteristic of subcutaneous administration and said $AUC_{Tmin-inf}$ being characteristic of intranasal administration without said mucosal permeation enhancer.

In the above aspect, said $T_{max}$ ranges from about 4.5 to about 15 minutes.

In the above aspect, said composition provides a $C_{max2}$ at a time of $T_{max2}$, said $T_{max2}$ being later than said $T_{max}$.

In the above aspect, said composition provides a $C_{min}$ at a time of $T_{min}$, said $T_{min}$ being later than said $T_{max}$ and earlier than said $T_{max2}$.

In the above aspect, wherein said mucosal permeation enhancer is alkyl glycoside or saccharide alkyl ester.

In the above aspect, the said alkyl glycoside or saccharide alkyl ester is selected from (1-O-n-Dodecyl-β-D-Maltopyranoside), tridecyl maltoside, sucrose monododecanoate, sucrose monotridecanoate and sucrose monotetradecanoate.

Specifically contemplated is pharmaceutical composition as described herein, which provides $AUC_{0-2}$ ranging from about 22 to 160 ng·h/mL.

Specifically contemplated is pharmaceutical composition as described herein, which provides $AUC_{0-6}$ ranging from about 25 to 160 ng·h/mL.

In one embodiment, each salt of sumatriptan, as defined above, is individually contemplated.

In another embodiment, aqueous solution of a salt of the present invention adapted for intranasal administration can have a pH in the range of about 4 to about 8. In another embodiment, the pH of aqueous solutions of the salt according to the invention for intranasal administration will be about 4.5 to about 7.5.

In another embodiment, the pH of an aqueous solution of a citrate salt of sumatriptan according to the invention for intranasal administration will be about about 4.5 to about 6.5, such as about 5 to about 6. Adjustment of the pH value of aqueous solutions of the sumatriptan salt to be within a desired range is conveniently effected by addition of a base, such as an inorganic base, such as an alkali metal hydroxide, including sodium or potassium hydroxide.

The aqueous solutions of the present invention may be prepared by dissolving the drug in water containing corresponding acid. For example, In one embodiment, solution can be prepared by admixture of 1 molar equivalent of sumatriptan and about 0.2 to 0.5 molar equivalent of concentrated phosphoric acid, or 0.30 molar equivalent of concentrated phosphoric acid, in water.

In another embodiment, solution can be prepared by admixture of 1 molar equivalent of sumatriptan and about 0.3 to about 0.6 molar equivalent of citric acid monohydrate, or about 0.43 molar equivalent of citric acid monohydrate, in water.

It will be appreciated that the precise therapeutic doses of the salt will depend on the age and condition of the patient and the nature of the condition to be treated, and will be in the ultimate discretion of the attendant physician.

However, in general effective doses for the treatment of conditions associated with cephalic pain, for example acute treatment of migraine, will lie in the range of about 0.5 to 100 mg, or about 1 to 60 mg, or about 2 to 40 mg of the active ingredient, per unit dose, which could be administered in single or divided doses, for example, 1 to 4 times per day.

The salt of the present invention may conveniently be presented in unit dose form. A convenient unit dose formulation for intranasal administration contains the active ingredient in an amount of about 0.5 mg to 100 mg, or about 1 to 60 mg, or about 2 to 40 mg, which may be administered into either one or both nostrils. In an embodiment, 2.5 mg to 25 mg of the active ingredient is administered in a single dose to one nostril.

A unit dose formulation may be provided as a single dose in a sealed unit, for example a vial of glass or plastic material which may be filled and sealed using conventional manufacturing techniques. Alternatively, a sealed vial of plastics material may be produced by form-fill-seal technology. In an embodiment, the vial and the components of the pharmaceutical formulation filled therein are heat stable. The sealed vial may be sterilized, for example by autoclaving at 120° C. for not less than 15 minutes, to provide a sterile unit dosage vial which can be assembled into a convenient delivery device prior to use. In another embodiment, the unit dose volume is 50 to 200 μL, for example 100 μL.

General Process-I:

A salt of sumatriptan may be prepared by dissolving sumatriptan, or a salt or a physiologically acceptable solvate thereof, in a solution of phosphoric acid or citric acid monohydrate. The process may be desirably carried out in aqueous media, optionally in the presence of an organic solvent such as an alcohol (for example, ethanol or isopropanol). Further, a salt of sumatriptan may be prepared by admixture of the sumatriptan base and phosphoric acid or citric acid monohydrate, in water.

General Process-II:

A salt of sumatriptan may be prepared by dissolving sumatriptan or a salt or solvate thereof in a solution of maleic acid, acetic acid, or formic acid. The process may be desirably carried out in aqueous media, optionally in the presence of an organic solvent such as an alcohol (for example, ethanol or isopropanol). Further, a salt of sumatriptan is prepared by admixture of sumatriptan base and formic acid, acetic acid or maleic acid, in water.

The pH of the product obtained is adjusted to about 4 to about 8, by the addition of sodium hydroxide or phosphate buffer.

In an alternative aspect of the present invention provides a pharmaceutical composition in a form adapted for intranasal administration, comprising an aqueous solution of sumatriptan or a physiologically acceptable salt or solvate thereof and an alkylglycoside or saccharide alkyl ester, wherein the solution has pH value in the range of about 4.5 to about 7.5.

Further alternative aspect of the present invention provides a method for the treatment of a mammal, including human being, suffering from or susceptible to cephalic pain, in particular migraine, which comprises intranasal administration of a pharmaceutical composition comprising an aqueous solution of sumatriptan or a physiologically acceptable salt or solvate thereof and an alkylglycoside or saccharide alkyl ester, wherein the solution has pH value in the range of about 5 to about 7.

Oral compositions may be associated with certain disadvantages in the treatment of conditions associated with cephalic pain. For example, such conditions, particularly migraine, are often accompanied by nausea which makes it difficult for a patient to take an oral composition. It is also highly desirable, particularly in the treatment of acute conditions, that pharmaceutical composition having high bioavailability and a rapid and consistent onset of action.

Rapid absorption can be achieved by parenteral administration (intravenous, subcutaneous, intraperitoneal, or intrarterial), but this may be unacceptable to some patients, especially if the drug is to be self-administered. Intranasal administration represents a convenient alternative route for administration.

Intranasal formulations may generally be provided in liquid or in dry powder forms. Satisfactory intranasal formulations must be sufficiently stable, chemically and physically, to be consistently dispensed in accurate metered doses, even after prolonged storage with potential temperature fluctuations of between 10 and 40° C. Accordingly, the active ingredient must be compatible with the excipients used in the formulation and should not aggregate in a manner which would result in a loss of accurate dose delivery, for example by precipitation from a liquid formulation or by caking of a powder formulation. To maximize retention of an intranasal formulation within the nasal passages of a patient after administration, particularly of a liquid formulation, it is desirable to deliver the unit dosage of active ingredient within a relatively small delivery volume, for example 50-200 µL, or 100 µL or less. This may necessitate the use of high concentrations of medicament and highly soluble active ingredients are therefore advantageous. Clearly, an active ingredient must also be presented in a form which is readily absorbed through the nasal mucosa but which is unassociated with any adverse effects such as irritancy.

Solutions of an active ingredient will generally be aqueous, for example prepared from water alone (for example sterile or pyrogen-free water), or water and a physiologically acceptable co-solvent (for example ethanol, propylene glycol, and polyethylene glycols such as PEG 400).

Such solutions may additionally-contain other excipients such as preservatives (for example benzalkonium chloride and phenylethyl alcohol), buffering agents, isotonicity-adjusting agents (for example sodium chloride), viscosity enhancing agents, absorption enhancers, flavoring agents (for example aromatic flavoring agents such as menthol, eucalyptol, camphor and methyl salicylate in amounts of about 0.001 to 0.5% w/w) and sweetening agents (for example saccharin in amounts of about 0.01% w/w to about 10% w/w, or in the range of about 1 to 5% w/w).

Solutions are applied directly to the nasal cavity by conventional means, for example with a dropper, pipette, or spray. The formulations may be provided in single- or multi-dose form. In the latter case, a means of dose metering is desirably provided. In the case of a dropper or pipette, this may be achieved by the patient administering an appropriate, predetermined volume of the solution. In the case of a spray, this may be achieved, for example, by means of a metering atomizing spray pump.

Intranasal administration may also be achieved by means of an aerosol formulation in which the compound is provided in a pressurized package with a suitable propellant such as a chlorofluorocarbon (CFC), for example dichlorodifluoromethane, trichlorofluoromethane or dichlorotetrafluoroethane, a hydrofluorocarbon (HFC), for example 1,1,1,2-tetrafluoroethane or 1,1,1,2,3,3,3-heptafluoropropane, carbon dioxide, or another suitable gas. The dose of drug may be controlled by provision of a metering valve.

In an embodiment, the invention includes use of packaging materials such as containers and closures of high-density polyethylene (HDPE), low-density polyethylene (LDPE) and or polypropylene and/or glass, glassine foil, aluminum pouches, and blisters or strips composed of aluminum or high-density polypropylene, polyvinyl chloride, polyvinylidene dichloride, etc.

The following examples further describe certain specific aspects and embodiments of the present invention and demonstrate the practice and advantages thereof. It is to be understood that the examples are given by way of illustration only and are not intended to limit the scope of the invention in any manner.

Preparation of citrate salt of Sumatriptan:

Added 130.0 grams (0.4406 mol) of Sumatriptan base to 1300 mL of ethanol in a round bottomed flask and heated the mixture under reflux temperature to get homogeneous solution. Added 97.2 grams (0.462 mol) of citric acid monohydrate and 1300 mL of ethanol solution to above reaction mixture at reflux. Maintained the reaction mixture at reflux temperature for 30 to 60 minutes. Cooled the reaction mixture to 25-35° C. and added 780 mL of Isopropanol and stirred for 15 to 30 minutes. Some gummy mass attached to the walls of the flask. Decanted solvent completely and added 2600 mL of isopropanol to the gummy mass and stirred for 2 to 4 hours. Filtered the solid and washed with 650 mL of Isopropanol. Added 2600 mL of Isopropanol to the wet solid and stirred for 2 to 4 hours. Filtered the solid and washed with 650 mL of Isopropanol. Dried the wet solid under reduced pressure at 50 to 60° C. till constant weight obtains. Yield:126.5 g HPLC: 99.72%, Assay by HPLC: 67.2% (Sumatriptan base), Moisture content: 2.0%, Assay by HPLC: 27.1% for Citric acid & 29.5% for Citric acid Monohydrate.

By following the similar methodology as described above other salts of sumatriptan can be prepared.

General Process for the Preparation of Salt Compositions:
Manufacturing Process:
Step-i: An acid of corresponding salt was dissolved in water
Step-ii: Sumatriptan was dissolved in the solution.
Step-iii: Phosphate buffer was added and mixed well and pH was checked and adjusted with sodium hydroxide (1N), if required.
Step-iv: The solution was filtered through a membrane filter and the pH was checked to maintain the pH range about 4 to about 8.

Step-v: Alkyl saccharide was dissolved in the solution. The solution was made to final volume with phosphate buffer and pH was again checked.

EXAMPLE-1

Preparation of 'Citrate salt of Sumatriptan' Composition

Procedure:

Step-i: Preparation of Phosphate buffer:
  0.2 grams of dibasic sodium phosphate & 10.0 grams of monobasic potassium phosphate was dissolved in sufficient water to produce 1000 mL.

Step-ii: Preparation of 1N Sodium hydroxide:
  Dissolve 1.0 gram of Sodium hydroxide was dissolved in sufficient water to produce 25 mL.

Step-iii: Preparation of 5N citric acid monohydrate:
  70.04 grams of citric acid monohydrate was dissolved in sufficient quantity of purified water and the volume was made up with purified water to 200 mL.

Step-iv: The required quantity of citric acid monohydrate (5N) solution was added to the required quantity of water and mixed well to get a uniform mixture. To this was added the required quantity of sumatriptan and the mixture was stirred to dissolve the drug.

Step-v: The pH of solution obtained in Step-iv was checked and required quantity of sodium hydroxide (1N) was added to it to adjust the pH of the solution to 5.5±0.5.

Step-vi: A required quantity of phosphate buffer was added to the solution of Step-v and was mixed well. The pH was checked and when 4 necessary was adjusted to the requisite value by adding a required quantity of sodium hydroxide (1N).

Step-vii: A required quantity of 1-O-n-Dodecyl-β-D-Maltopyranoside was added to a solution of Step-vi and mixed well till it dissolved completely. The volume was made up with phosphate buffer and the resulting solution was mixed well.

Step-viii: The solution of Step-vii was filtered through a membrane filter by SS Filtration assembly.

Step-ix: The required quantity of solution of Step-viii was filled in a nasal spray device.

| S. No. | Ingredient | Qty/Unit dose (mg/100 µl) | | | |
|---|---|---|---|---|---|
| | | For 5 mg | For 10 mg | For 15 mg | For 20 mg |
| 1 | Sumatriptan | 5.00 mg | 10.00 mg | 15.00 mg | 20.00 mg |
| 2 | Citric acid monohydrate * | 1.576 mg | 3.152 mg | 4.728 | 6.304 mg |
| 3 | 1-O-n-Dodecyl-β-D-Maltopyranoside | 0.20 mg | 0.20 mg | 0.20 mg | 0.20 mg |
| 4 | Sodium hydroxide | q.s. to adjust pH 5.0-6.0 | q.s. to adjust pH 5.0-6.0 | q.s. to adjust pH 5.0-6.0 | q.s. to adjust pH 5.0-6.0 |
| 5 | Purified water | 20.000 µl | 20.000 µl | 20.000 µl | 20.000 µl |
| 6 | Phosphate Buffer ** | q.s. to 100 µl | q.s. to 100 µl | q.s. to 100 µl | q.s. to 100 µl | q.s.—quantum sufficient
* To be used as (5N) Citric acid solution in purified water.
** Contains Dibasic sodium phosphate and Monobasic potassium phosphate and to be mixed in the ratio of 1:50 in purified water for the preparation of Phosphate buffer.

EXAMPLE-2

Preparation of 'Phosphate Salt of Sumatriptan' Composition

Pharmaceutical composition comprising phosphate salt of Sumatriptan is prepared by similar procedure as described in Example-1, with the following quantities of the reacting materials.

| Ingredient/Condition | Quantity/Value |
|---|---|
| Sumatriptan | 20 mg |
| 1-O-n-Dodecyl-β-D-Maltopyranoside | 0.2 mg |
| Phosphoric acid | 4.03 µL |
| Citric acid monohydrate | — |
| Sodium hydroxide | q.s. |
| Water | 20 µL |
| Phosphate buffer | q.s. to 100 µL |
| pH | 6.5-7.5 |

EXAMPLES 3-5

Preparation of 'formate, acetate and maleate salts of Sumatriptan' Composition

The compositions of Formate, Acetate and Maleate salt of Sumatriptan composition can be prepared by following the procedure as described in Example-I by taking appropriate quantities of the reacting substances and by maintaining appropriate suitable pH conditions.

| S. No | Ingredients | Composition of Example-3 | Composition of Example-4 | Composition of Example-5 |
|---|---|---|---|---|
| 1 | Sumatriptan | 20.00 mg | 20.00 mg | 20.00 mg |
| 2 | Formic acid * | 2.55 µl | NA | NA |
| 3 | Acetic acid ** | NA | 3.80 µl | NA |
| 4 | Maleic acid *** | NA | NA | 3.86 mg |
| 5 | 1-O-n-Dodecyl-β-D-Maltopyranoside | 0.2 mg | 0.2 mg | 0.2 mg |
| 6 | Phosphate buffer | 100 µl | 100 µl | 100 µl |
| | pH observed for final solution | 6.96 | 5.49 | 7.05 |

* To be used as (10N) Formic acid solution in water.
** To be used as (10N) Acetic acid solution in water.
*** To be used as (5N) Maleic acid solution in water.

EXAMPLE-6

Sumatriptan Citrate Salt Composition

Composition comprising Sumatriptan Citrate salt was prepared by following procedure:

Step-i: Preparation of Phosphate buffer: Dissolved 0.2 grams of dibasic sodium phosphate & 10.0 grams of monobasic potassium phosphate in sufficient water to produce 1000 mL.

Step-ii: Preparation of 1N Sodium hydroxide: Dissolved 1.0 gram of Sodium hydroxide in required quantity of water and dilute with water to 25 mL.

Step-iii: Added the required quantity of Sumatriptan-Citric acid monohydrate complex to required quantity of water and mix well until it dissolves.

Step-iv: Checked the pH of solution of step-iv and added required quantity of sodium hydroxide (1N) to it to adjust the pH of the solution to 5.5±0.5.

Step-v: Added required quantity of phosphate buffer to solution of step-iv and mix well. Checked the pH and if necessary and added required quantity of sodium hydroxide (1N) to adjust the pH of the solution to 5.5±0.5.

Step-vi: Added required quantity of n-Dodecyl-beta-D-Maltopyranoside to solution of step-v and mixed well till it dissolves completely. Made up the volume with phosphate buffer and mixed well.

| Step-vii: | Item Name | Qty/Unit dose (Qty/100 μL) |
|---|---|---|
| 1 | Sumatriptan-Citric acid salt* | 22.32 mg |
| 2 | n-Dodecyl-beta-D-Maltopyranoside | 0.20 mg |
| 3 | Sodium hydroxide | q.s. to adjust pH 5.0-6.0 |
| 4 | Purified water | 20.00 μl |
| 5 | Phosphate buffer ** | q.s. to 100 μL |

EXAMPLE-7

Other Sumatriptan Salt Compositions

By taking appropriate Sumatriptan salt, pharmaceutical compositions can be prepared by following the procedure as described in Example-6.

EXAMPLE-8

Clinical Trials Data

Figure 4:
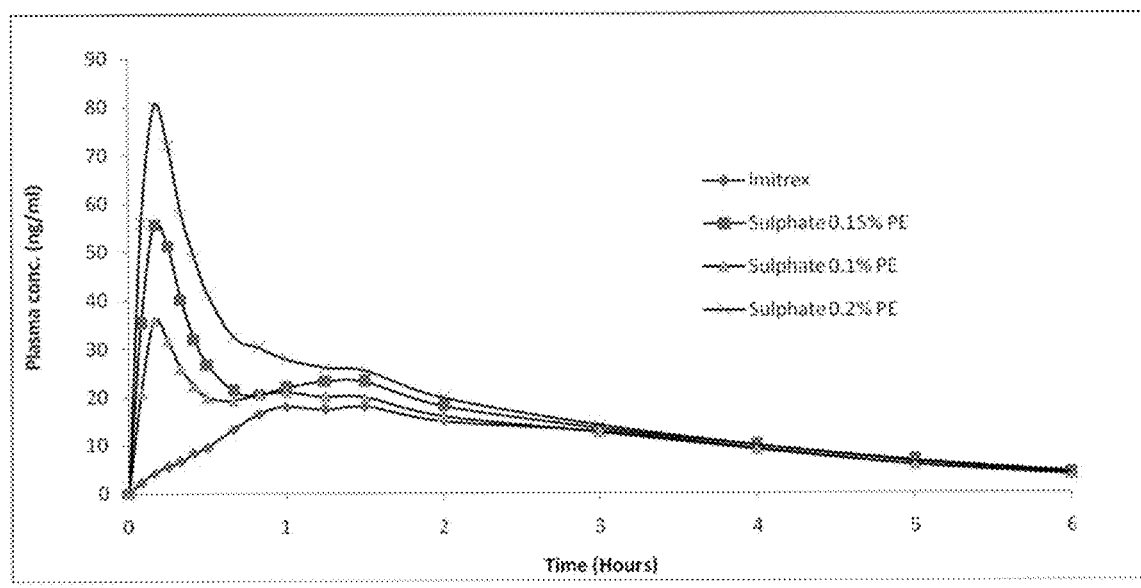
FIG.-4 shows a comparision of the average plasma concentration of all patients at various time points as indicated for the Imitrex® nasal spray reference and Sulphate salt of Sumatriptan (Sulphate) upon intranasal administration of the pharmaceutical formulation comprising 0.1%, 0.15% & 2.0% concentrations of Permeation Enhancer (PE) respectively'.

Study-1: 4-way crossover study of intranasal administration of sulphate salt of sumatriptan with Test-1, Test-2, Test-3 having the permeation enhancer in concentrations of 0.1%, 0.15%, 0.2% respectively and Imitrex® 20 mg as the reference product (Refer FIG.-4)

(Number of subjects completed study (n)=21).

Each drug solution (Test-1, Test-2, Test-3 and Reference) is administered to 24 patients in a three-way crossover study, with a washout period between doses of at least 7 days, as a 100 microliter metered nasal spray using standard metered nasal spray devices such as those manufactured by Ing. Erich Pfeiffer GmbH, Radolfzell, Germany, Valois Pharma, Le Neubourg, France, or Becton Dickinson, New Jersey, USA. Blood samples are collected from each patient at the timed intervals, for example 0.08, 0.17, 0.25, 0.33, 0.42, 0.6, 0.67, 0.83, 1, 2, 3, 4, 6, 8, 12, 24 hours.

Sample for Test-1: Sulphate salt of Sumatriptan composition 20 mg Nasal spray (a final sumatriptan concentration of 20 mg per 100 microliter spray and having about 0.1% of permeation enhancer (dodecyl maltoside)), manufactured by Dr. Reddy's Laboratories Ltd., India.

Sample for Test-2: Sulphate salt of Sumatriptan composition 20 mg Nasal spray (a final sumatriptan concentration of 20 mg per 100 microliter spray and having about 0.15% of permeation enhancer (dodecyl maltoside)), manufactured by Dr. Reddy's Laboratories Ltd., India.

Sample for Test-3: Sulphate salt of Sumatriptan composition 20 mg Nasal spray (a final sumatriptan concentration of 20 mg per 100 microliter spray and having about 0.2% of permeation enhancer (dodecyl maltoside)), manufactured by Dr. Reddy's Laboratories Ltd., India.

Reference: Imitrex® (Sumatriptan) nasal spray, 20 mg per 100 microliters), manufactured by GlaxoSmithKline.

EXAMPLE-9

Figure 2:
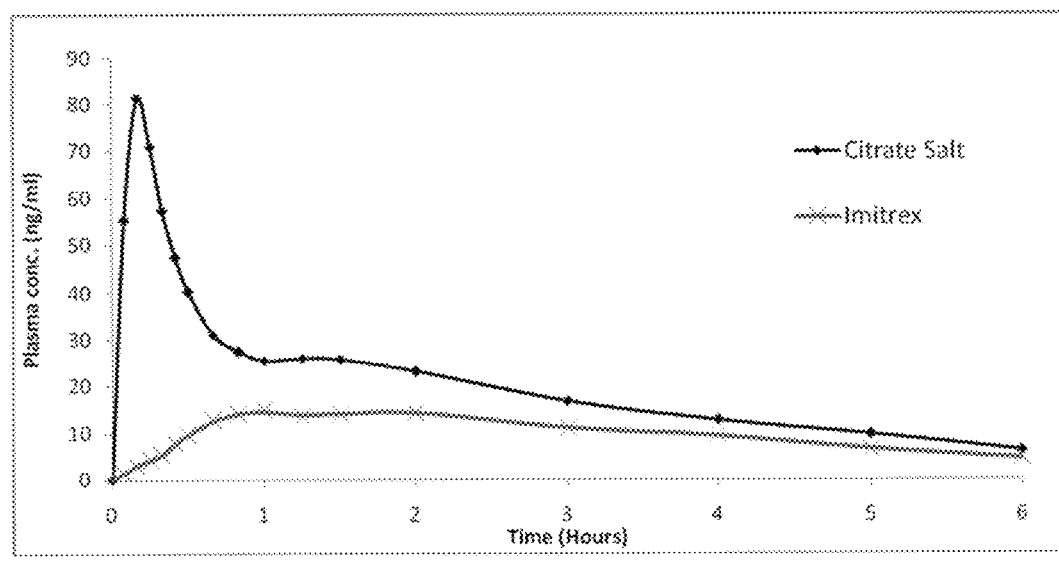
FIG.-2 shows a comparison of the average plasma levels of all patients at the various time points as indicated for the Imitrex® nasal spray reference and Citrate salt of Sumatriptan pharmaceutical composition described herein.
Figure 3:
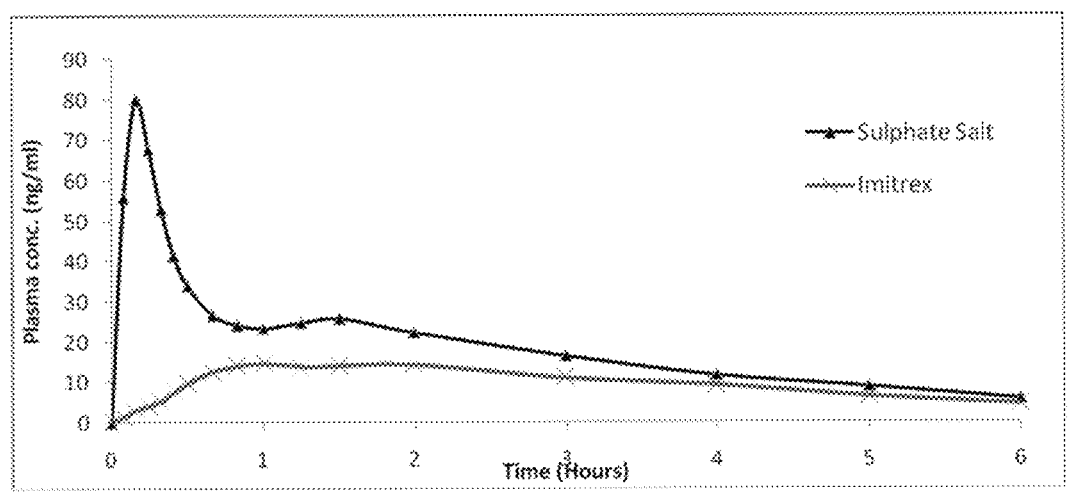
FIG.-3 shows a comparison of the average plasma levels of all patients at the various time points as indicated for the Imitrex® nasal spray reference and Sulphate salt of Sumatriptan pharmaceutical composition described herein.

Study-2: 3-way crossover study of intranasal administration of various sumatriptan salts (phosphate, citrate and sulphate) having 0.2% of the permeation enhancer (Refer FIG.-1, FIG.-2 and FIG.-3 respectively)

(Number of subjects completed study (n)=15)

Each drug solution (phosphate, citrate and sulfate salt of sumatriptan) is administered to 18 patients in a three-way crossover study, with a washout period between doses of at least 8 days, as a 100 microliter metered nasal spray using standard metered nasal spray devices such as those manufactured by Ing. Erich Pfeiffer GmbH, Radolfzell, Germany, Valois Pharma, Le Neubourg, France, or Becton Dickinson, N.J., USA. Blood samples are collected from each patient at the timed intervals, for example 0.08, 0.17, 0.25, 0.33, 0.42, 0.6, 0.67, 0.83, 1, 2, 3, 4, 6, 8, 12, 24 hours.

Phosphate salt of Sumatriptan composition 20 mg Nasal spray (a final sumatriptan concentration of 20 mg per 100 microliter spray and having about 0.2% of permeation enhancer (dodecyl maltoside)), manufactured by Dr. Reddy's Laboratories Ltd., India.

Citrate salt of Sumatriptan composition 20 mg Nasal spray (a final sumatriptan concentration of 20 mg per 100 microliter spray and having about 0.2% of permeation enhancer (dodecyl maltoside)), manufactured by Dr. Reddy's Laboratories Ltd., India.

Sulphate salt of Sumatriptan composition 20 mg Nasal spray (a final sumatriptan concentration of 20 mg per 100 microliter spray and having about 0.2% of permeation enhancer (dodecyl maltoside)), manufactured by Dr. Reddy's Laboratories Ltd., India.

EXAMPLE-10

Study-3: 3-way crossover study of intranasal administration of sulphate salt of sumatriptan with Test-1 having about 0.2% of permeation enhancer; Test-2 without permeation enhancer and Imitrex® as the reference product (Number of subjects completed study (n)=15)

Each drug solution (Test-1, Test-2 and Reference samples) is administered to 18 patients in a three-way crossover study, with a washout period between doses of at least 4 days, as a 100 microliter metered nasal spray using standard metered nasal spray devices such as those manufactured by Ing. Erich Pfeiffer GmbH, Radolfzell, Germany, Valois Pharma, Le Neubourg, France, or Becton Dickinson, N.J., USA. Blood samples are collected from each patient at the timed intervals, for example 0.08, 0.17, 0.25, 0.33, 0.42, 0.6, 0.67, 0.83, 1, 2, 3, 4, 6, 8, 12, 24 hours.

Sample used in Test-1: Sulfate salt of Sumatriptan composition 20 mg Nasal spray (a final sumatriptan concentration of 20 mg per 100 microliter spray and having about 0.2% of permeation enhancer (dodecyl maltoside)), manufactured by Dr. Reddy's Laboratories Ltd., India.

Sample used in Test-2: Sulfate salt of Sumatriptan composition 20 mg Nasal spray (a final sumatriptan concentration of 20 mg per 100 microliter spray and without permeation enhancer), manufactured by Dr. Reddy's Laboratories Ltd., India.

Reference: Imitrex® (Sumatriptan) nasal spray, 20 mg per 100 microliters), manufactured by GlaxoSmithKline,

TABLE 1

Area under the plasma concentration versus time curve from time 0 to infinity ($AUC_{0\text{-}inf}$)

| | $AUC_{0\text{-}inf}$ (ng · h/mL) | | | | |
|---|---|---|---|---|---|
| Statistics | Study3 (0.2%) | Study2 (Sulphate salt) | Study1 (0.2%) | Study2 (Phosphate salt) | Study2 (Citrate salt) |
| Arithmetic Mean | 114.70 | 135.52 | 125.18 | 107.67 | 142.57 |
| Standard Deviation | 52.98 | 48.78 | 46.72 | 25.03 | 45.83 |
| Max | 222.44 | 201.58 | 201.46 | 169.32 | 258.86 |
| Median | 109.04 | 130.73 | 117.94 | 108.22 | 136.85 |
| Min | 33.45 | 50.91 | 14.81 | 63.08 | 80.16 |
| G. Mean | 101.68 | 125.64 | 112.78 | 104.98 | 136.27 |
| CV % | 46.19 | 36.0 | 37.33 | 23.25 | 32.15 |

TABLE 2

Peak plasma concentration for sumatriptan ($C_{max}$)

| | $C_{max}$ (ng/mL) | | | | |
|---|---|---|---|---|---|
| Statistics | Study3 (0.2%) | Study2 (Sulphate salt) | Study1 (0.2%) | Study2 (Phosphate salt) | Study2 (Citrate salt) |
| Arithmetic Mean | 60.50 | 84.98 | 83.69 | 44.78 | 85.30 |
| Standard Deviation | 31.93 | 57.79 | 46.44 | 17.18 | 34.56 |
| Max | 110.88 | 213.11 | 173.43 | 81.22 | 186.33 |
| Median | 67.48 | 85.30 | 78.35 | 40.26 | 86.65 |
| Min | 8.44 | 15.62 | 5.95 | 22.69 | 48.62 |
| G. Mean | 48.65 | 67.68 | 67.54 | 41.96 | 79.95 |
| CV % | 55.05 | 68.01 | 55.50 | 38.37 | 40.52 |

TABLE 3

Time to peak plasma concentration for sumatriptan ($T_{max}$)

| | $T_{max}$ (h) | | | | |
|---|---|---|---|---|---|
| Statistics | Study3 (0.2%) | Study2 (sulphate salt) | Study1 (0.2%) | Study2 (Phosphate salt) | Study2 (Citrate salt) |
| Arithmetic Mean | 0.21 | 0.24 | 0.21 | 0.43 | 0.161 |
| Standard Deviation | 0.13 | 0.28 | 0.18 | 0.55 | 0.05 |
| Maximum | 0.66 | 1.25 | 1.00 | 0.25 | 0.25 |
| Median | 0.167 | 0.167 | 0.167 | 0.167 | 0.167 |
| Minimum | 0.083 | 0.083 | 0.083 | 0.083 | 0.083 |
| CV % | 62.97 | 114.74 | 84.84 | 127.76 | 30.76 |

TABLE 4

Area under the plasma concentration versus time curve from time 0 to Tmax ($AUC_{0\text{-}Tmax}$)

| | $AUC_{0\text{-}Tmax}$ (ng · h/mL) | | | | | |
|---|---|---|---|---|---|---|
| Statistics | Study3 (0.2%) | Study2 (Sulphate salt) | Study1 (0.2%) | Study2 (Phosphate salt) | Study2 (Citrate salt) | Study3 (Imitrex 20 mg) |
| G. Mean | 4.51 | 5.99 | 6.22 | 3.39 | 12.99 | 13.54 |
| Arithmetic Mean | 6.05 | 7.93 | 7.95 | 3.72 | 13.63 | 14.36 |
| 95% CI | 4.3-7.8 | 4.9-11.0 | 6.0-9.9 | 3.0-4.5 | 11.6-15.7 | 12.2-16.5 |

TABLE 5

Ratio of $C_{max}$ to $AUC_{0\text{-}inf}$ ($C_{max}/AUC_{0\text{-}inf}$)

| | $C_{max}/AUC_{0\text{-}inf}$ | | | | |
|---|---|---|---|---|---|
| Statistics | Study3 (0.2%) | Study2 (Sulphate salt) | Study1 (0.2%) | Study2 (Phosphate salt) | Study2 (Citrate salt) |
| G. Mean | 0.47 | 0.53 | 0.59 | 0.18 | 0.47 |
| Arithmetic Mean | 0.52 | 0.62 | 0.66 | 0.41 | 0.59 |
| 95% CI | 0.5-0.54 | 0.5-0.71 | 0.6-0.71 | 0.37-0.44 | 0.57-0.62 |

TABLE 6

Area under the plasma concentration versus time curve from time 0 to 2 hours ($AUC_{0\text{-}2}$)

| | $AUC_{0\text{-}2}$ (ng · h/mL) | | |
|---|---|---|---|
| Statistics | Study2 (Sulphate salt) | Study2 (Phosphate salt) | Study2 (Citrate salt) |
| A. Mean | 63.81 | 44.97 | 68.07 |
| Std. Dev | 27.92 | 11.11 | 29.59 |
| Max | 116.49 | 60.80 | 156.13 |
| Median | 69.08 | 46.57 | 61.11 |
| Min | 22.05 | 25.79 | 38.39 |
| G. Mean | 57.16 | 43.58 | 63.49 |
| CV % | 43.75 | 24.72 | 43.48 |

TABLE 7

Area under the plasma concentration versus time curve from time 0 to 6 hours ($AUC_{0\text{-}6}$)

| | $AUC_{0\text{-}6}$ (ng · h/mL) | | |
|---|---|---|---|
| Statistics | Study2 (Sulphate salt) | Study2 (Phosphate salt) | Study2 (Citrate salt) |
| A. Mean | 68.08 | 88.98 | 44.97 |
| Std. Dev | 29.60 | 21.87 | 11.12 |
| Max | 156.13 | 142.27 | 60.80 |
| Median | 61.12 | 91.46 | 46.58 |
| Min | 38.39 | 55.32 | 25.79 |
| G. Mean | 63.50 | 86.50 | 43.59 |
| CV % | 43.48 | 24.58 | 24.72 |

We claim:

1. A method of treating a human suffering from or susceptible to cephalic pain comprising intranasal administration of a composition comprising citric acid salt of sumatriptan, or a physiologically acceptable solvate thereof, an alkyl glycoside or saccharide ester and optionally a pharmaceutically acceptable excipient, wherein, said composition provides a $T_{max}$ substantially equivalent to subcutaneous administration of said sumatriptan.

2. The method as claimed in claim 1, wherein said composition provides $T_{max}$ value of less than 30 minutes.

3. The method as claimed in claim 1, wherein said composition provides $T_{max}$ value ranging from about 4 minutes to about 15 minutes.

4. The method as claimed in claim 1, wherein said alkyl glycoside or saccharide alkyl ester is selected from dodecyl maltoside (1-O-n Dodecyl-β-D-Maltopyranoside), tridecyl maltoside, sucrose monododecanoate, sucrose monotridecanoate and sucrose monotetradecanoate.

5. The method as claimed in claim 4, wherein said alkyl glycoside or saccharide alkyl ester is dodecyl maltoside (1-O-n-Dodecyl-β-D-Maltopyranoside).

6. The method as claimed in claim 1, wherein said composition upon nasal administration provides a ratio of $C_{max}$ to $AUC_{0-inf}$ of at least about 0.3.

7. The method as claimed in claim 1, wherein said alkyl glycoside or saccharide alkyl ester is present in a concentration of from about 0.05 to about 3.0%.

8. The method as claimed in claim 7, wherein said alkyl glycoside or saccharide alkyl ester is present in a concentration of at least about 0.1%.

9. The method as claimed in claim 1, wherein said composition upon nasal administration provides $AUC_{0-2}$ ranging from about 22 to about 160 ngh/mL.

10. The method as claimed in claim 1, wherein said composition upon nasal administration provides $AUC_{0-6}$ ranging from about 25 to about 160 ngh/mL.

11. The method as claimed in claim 1, wherein said human is suffering from or susceptible to migraine or cluster headache.

12. A method of treating a human suffering from or susceptible to cephalic pain comprising intranasal administration of composition comprising citric acid salt of sumatriptan or a physiologically acceptable solvate thereof, an alkyl glycoside or saccharide alkyl ester and optionally a pharmaceutically acceptable excipient, wherein said composition a $T_{max}$ value of less than or equal 15 minutes.

13. The method as claimed in claim 12, wherein said composition provides a $T_{max}$ substantially equivalent to subcutaneous administration of said sumatriptan.

14. The method as claimed in claim 12, wherein said composition upon nasal administration provides $AUC_{0-2}$ ranging from about 22 to about 160 ngh/mL.

15. The method as claimed in claim 12, wherein said composition upon nasal administration provides $AUC_{0-6}$ ranging from about 25 to about 160 ngh/mL.

16. The method as claimed in claim 12, wherein said composition upon nasal administration provides a ratio of $C_{max}$ to $AUC_{0-inf}$ of at least about 0.3.

17. The method as claimed in claim 12, wherein said alkyl glycoside or saccharide alkyl ester is selected from dodecyl maltoside (1-O-n-Dodecyl-β-D-Maltopyranoside), tridecyl maltoside, sucrose monododecanoate, sucrose monotridecanoate and sucrose monotetradecanoate.

18. The method as claimed in claim 12, wherein said alkyl glycoside or saccharide alkyl ester is present in a concentration of from about 0.05 to about 3.0%.

19. The method as claimed in claim 17, wherein said alkyl glycoside or saccharide alkyl ester is present in a concentration of at least about 0.1%.

20. The method as claimed in claim 12, wherein said human is suffering from or susceptible to migraine or cluster headache.

\* \* \* \* \*